United States Patent [19]

Weiss

[11] Patent Number: 4,699,768
[45] Date of Patent: Oct. 13, 1987

[54] APPARATUS FOR EXCHANGING SUBSTANCES BETWEEN FLUIDS

[75] Inventor: Charles B. Weiss, Amsterdam, N.Y.

[73] Assignee: Technicon Instruments Corporation, Tarrytown, N.Y.

[21] Appl. No.: 530,514

[22] Filed: Sep. 9, 1983

[51] Int. Cl.[4] .......................................... G01N 30/02
[52] U.S. Cl. ........................................ 422/70; 55/197;
      55/386; 210/198.2; 422/169; 422/82; 436/53;
      436/161
[58] Field of Search ..................... 422/68, 70, 82, 101,
      422/69; 436/53, 161; 55/197, 386; 210/198.2;
      202/160; 203/1, 2

[56] References Cited

U.S. PATENT DOCUMENTS

| | | | |
|---|---|---|---|
| 3,199,956 | 8/1965 | Ferrari | 422/62 |
| 3,224,499 | 12/1965 | Reinecke | 55/386 |
| 3,399,972 | 9/1968 | Skeggs et al. | 422/70 |
| 3,422,665 | 1/1969 | Haase | 55/197 |
| 3,457,708 | 7/1969 | Deford | 55/386 |
| 3,735,565 | 5/1973 | Gilby et al. | 55/197 |
| 4,028,194 | 6/1977 | Boyd | 202/160 |
| 4,180,389 | 12/1979 | Paul | 55/197 |

Primary Examiner—Michael S. Marcus
Attorney, Agent, or Firm—Jeffrey M. Greenman; James J. Romano, Jr.

[57] ABSTRACT

Apparatus and method are provided for the exchange of substances between substance carrier and recovery fluids in predetermined carrier/recovery fluid volumetric ratios, and operate through the vaporization of the carrier fluid in a separation chamber to separate the substance therefrom at a separation zone therein and effect the deposition and accumulation of the substance in a relatively narrow band, and the subsequent recovery of the substance band from the separation chamber by the substance recovery fluid. Correlation of the carrier fluid flow rate into the separation chamber, and the separation chamber temperature, is effective to determine the location of the substance band in the separation chamber. Segmentation of the substance carrier and recovery fluids materially increases the efficiency of the separation and recovery processes. The apparatus and method are particularly adapted for high operational rate operation on an automated basis; and are adapted for operation on a batch basis.

12 Claims, 4 Drawing Figures

APPARATUS FOR EXCHANGING SUBSTANCES BETWEEN FLUIDS

BACKGROUND OF THE INVENTION

1. Field of the Invention

This invention relates to new and improved apparatus and method for exchanging substances between the same or different substance carrier and substance recovery fluids, by separation of the substance from the former and recovery by the latter, in predetermined substance carrier/substance recovery fluid volumetric ratios; particularly as applied to substances which are constituted by analytes, and carrier and recovery fluids which are constituted by solvents.

2. Description of the prior art

Although a variety of prior art apparatus and methods are known for the purposes disclosed herein, none are known to be configured and operable in the manners of those of this invention, or to provide the combination of particularly significant advantages as are provided by the latter. Most relevantly, the solvent concentrator disclosed in FIG. 3 of paper by D. Keuhl, et al., entitled "Novel Approaches To Interfacing A High Performance Liquid Chromatograph With A Fourier Transform Infrared Spectrometer," *Journal of Chromatographic Science*, Volume 17, August 1979, pages 471–476, although operable to the same general purposes as those of this invention insofar as substance concentration per se is concerned, is nonetheless quite remote therefrom in lacking the capability to deposit the substance of interest in a narrow compressed band at a predeterminable location in the light pipe concentrating tube because the substance must be sprayed into the concentrating tube. Further, although substance recovery in small recovery fluid volumes might be possible in this prior art concentrator, the same would require the use of very small concentrator tubes with attendant significant reduction in tube surface area and resultant very low substance concentration rates.

Also relevant, but to a somewhat lesser degree, are the basic "purge and trap" substance concentration apparatus and methods of the prior art as disclosed for example in U.S. Pat. No. 4,180,389, and embodied for example in the CDS GC Sample Concentrators as manufactured by Chemical Data Systems, Inc. of Chicago, Ill., the Trace Organics Concentrators as manufactured by Valco Instruments Systems, Inc. of Houston, Tex., and the Trace Enrichment Systems as manufactured by Bioanalytical Systems, Inc. of Lafayette, Ind.; which, although operable to the same general purposes as the apparatus and method of this invention insofar as substance concentration per se is concerned, are nonetheless quite remote therefrom in requiring desorption on one or more adsorbent traps, and repeated backflushing and/or reverse trap heating or like procedures to, in any event, significantly limit the range of applications thereof.

Of limited relevance are the zone refining techniques of the prior art, as disclosed for example in paper of V. L. Poland entitled "Zone Refining, What it can do for you?" Intek (in-house publication of Abbott Laboratories, Chicago, Ill.) Vol. 6, Number 11, November 1970, pages 1–3; which, although capable of ultimately effecting very high substance concentrations, are even more remote from the apparatus and method of this invention. More specifically, these techniques separate by relating melting points as a function of the relative compositions of a solid and molten state, rather than as a function of relative vapor pressures; and require, for example, laborious repeated passes of the carrier of the substance to be concentrated relative to heating means to effect the requisite plurality of concentrating zone passes and the desired high degree of substance concentration.

In addition, and with the exception of the CDS Concentrators, the relevant prior art apparatus and methods under discussion will generally be found to be configured for operation on what is essentially a batch basis and thus not particularly, if at all, adaptable as a practical matter for operation attendant the automated analysis of a series of samples on a continuous flow successive basis in accordance with contemporary automated sample analysis procedures and devices.

OBJECTS OF THE INVENTION

It is, accordingly, an object of this invention to provide new and improved apparatus and method for exchanging substances between the same or different substance carrier and substance recovery fluids in predetermined substance carrier/ substance recovery fluid volumetric ratios.

Another object of this invention is the provision of apparatus and method as above which are operable with very high degrees of effectiveness and precision.

Another object of this invention is the provision of apparatus and method as above with relatively high operational rates.

Another object of this invention is the provision of apparatus and method as above which are extremely versatile in application.

Another object of this invention is the provision of apparatus and method as above which, when applied to substance concentration between carrier and recovery fluids, are operable to effect particularly high levels of substance concentration in the substance recovery fluid.

Another object of this invention is the provision of apparatus and method as above which are of relatively simple configuration and manner of operation, and which require the use of only relatively low cost components of ready availability and proven dependability to thus provide for relatively low apparatus cost, and long periods of reliable and satisfactory apparatus operation.

A further object of this invention is the provision of apparatus and method as above which are particularly adapted to utilization attendant the automated analysis of a series of samples on a continuous flow, successive sample analysis basis.

SUMMARY OF THE INVENTION

The new and improved apparatus and method of the invention comprise vaporizer-collector means including separation chamber means which are operable, when heated above the boiling point of the substance carrier fluid but below the boiling point of the substance, to vaporize the former attendant its flow therethrough to effect separation of the substance therefrom. The flow rate of the substance carrier fluid through the vaporizer-collector means, and the temperature to which the latter is heated, are correlated to effect the deposition and accumulation of the substance in a narrow compressed band at a pre-determinable location on the interior wall surface or a matrix of the vaporizer-collector means. Subsequent cooling of the vaporizer-collector means below the boiling point of the substance recovery fluid, and flow of the latter therethrough is operable to effectively remove the substance from the vaporizer-collector means into the substance recovery fluid for flow therewith out of the vaporizer-collector means. Means are provided to segment both the substance carrier and recovery fluids with a segmenting fluid to materially assist in effective substance deposition and removal; and provision is made to utilize the segmenting fluid, per se, and the substance recovery fluid, to periodically purge the vaporizer-collector means. The apparatus and method of the invention are operable at relatively high rates with a wide variety of substances, and with a wide variety of the same or different substance carrier and recovery fluids; and are operable to exchange the substance between the substance carrier and recovery fluids in any reasonable substance carrier fluid/substance recovery fluid volumetric ratio; thereby providing a very high level of applicational versatility. The apparatus and method are operable on a batch basis; and are operable attendant the automated analysis of a series of samples on a continuous flow, successive sample analysis basis.

BRIEF DESCRIPTION OF THE DRAWINGS

The above and other objects and significant advantages of this invention are believed made clear by the following detailed description thereof taken in conjunction with the accompanying drawings wherein:

FIG. 1 is a schematic diagram of a first embodiment of the invention depicted in conjunction with automated sample supply and sample analysis apparatus to illustrate the particular adaptability of the invention to automation;

FIG. 2 is a fragmentary perspective view of the concentrating column of the apparatus of FIG. 1;

FIG. 3 is a schematic diagram of the relevant portion of a second embodiment of the invention; and FIG. 4 is a schematic diagram of the relevant portion of a third embodiment of the invention.

DETAILED DESCRIPTION OF THE INVENTION

Referring now to FIG. 1, a first embodiment of apparatus constructed and operative in accordance with the teachings of this invention is indicated generally at 10; and comprises generally vertically oriented heating-cooling means taking the form of a vaporizer-collector 12, and serially connected, generally vertically oriented cooling means taking the form of a condensor 14 which are spaced as shown from vaporizer-collector 12. The vaporizer-collector 12 comprises a generally elongate, outer temperature control jacket 16 and a conduit 18 extending generally co-axially thereof and including a helically coiled section 20 which forms a substance separation chamber. In like manner, the condensor 14 comprises a generally elongate outer temperature control jacket 22, and a conduit 24 extending generally co-axially thereof and including a helically coiled section 26. Conduits 18 and 24 are connected as shown between the outer jackets 16 and 22 by connecting means 28 which may, for example, take the form of an appropriately inert fluid-tight and resilient SwageLock Teflon fitting.

Outer jacket 16 comprises spaced, temperature control fluid inlet and outlet 30 and 32, respectively; and outer jacket 22 comprises spaced, temperature control fluid inlet and outlet 34 and 36, respectively.

Temperature control means are indicated generally at 38 and comprise heating fluid supply means and cooling fluid supply means, as respectively schematically indicated at 40 and 42; and thermo-hydraulic switching circuit means as schematically indicated at 44 which are operative to selectively connect the heating and cooling fluid supply means 40 and 42 to outer jacket 16 and outer jacket 22.

The heating fluid supply means 40 may, for example, take the form of a thermostatically controlled Haake Constant Temperature Bath and Circulator, as manufactured by Haake, Inc. of Saddle River, N.J., which is operable to heat and maintain a self-contained supply of an appropriate fluid such as water precisely to and at a preselected temperature within a broad available temperature range (for example from $+20°$ C. to $+150°$ C. within $\pm 0.02°$ C.) and to circulate that fluid on demand precisely at an appropriate flow rate of, for example, 10 liters/min. In addition, temperature control apparatus of this nature exhibit sufficient power output so that the temperature of the vaporizer-collector 12 does not drop appreciably during the vaporization phase as described in greater detail hereinbelow.

The cooling fluid supply means 42 may, for example, simply take the form of any readily available "cold" water tap.

The thermo-hydraulic switching circuit means 44 comprise conduit 50, three-way valve 52, conduit 54, conduit junction 56, and conduit 58 which connect the outlet of heating fluid supply means 40 to the inlet 30 of outer jacket 16. Conduit 60, conduit junction 61, conduit 59, valve 62 and conduit 64 connect cooling fluid supply means 42 to conduit junction 56; while conduit 63 connects conduit junction 61, and thus the cooling fluid supply means 42, to inlet 34 of outer jacket 22. Conduit 66, three-way valve 68, conduit 69, conduit junction 70 and conduit 72 connect outer jacket outlet 32 to the inlet of heating fluid supply means 40, and a bypass conduit 74 connects valve 52 to conduit junction 70; while conduits 76 and 78 respectively connect valve 68 and outlet 36 of outer jacket 22 to drain as indicated.

Substance carrier and recovery fluids supply means are indicated generally at 80 in FIG. 1, and comprise an appropriate source 82 of the substance recovery fluid. The substance carrier fluid supply means may, for example, take the form of automatic sample fluid supply apparatus, of the nature disclosed in U.S. Pat. No. 3,038,340, as indicated schematically at 84 in FIG. 1, but with somewhat increased fluid supply capacity. In such instance, supply means 84 would be configured and operable to automatically supply a series of like volumes of substance carrier fluids in sequence for processing by apparatus 10. Substance carrier fluid supply means 84 do not, per se, form part of this invention. Conduits 83 and 85 respectively connect sources 82 and 84 to three-way valve 86. A variable speed pump is indicated at 88 and preferably takes the form of a positive displacement HPLC piston pump with substantial resistance to corrosive fluids in the nature of solvents. Conduit 90 connects valve 86 to the inlet of pump 88.

Segmenting fluid supply means are indicated generally at 92 in FIG. 1 and comprise a pressurized source 94 of an appropriate segmenting fluid connected as shown by conduit 96, pressure regulator 98, and conduit 100, respectively, to an injection valve capable of pulsing, or open operation, as required. A segmentation fitting is indicated at 104, and conduits 106 and 108 respectively connect supply valve 102 and the outlet of pump 88 to the fitting inlets. Conduit 110 connects the outlet of fitting 104 to the inlet of vaporizer-collector conduit 18, and connector 120 of the nature described hereinabove is provided to positively seal and maintain the conduit juncture while enabling limited relative movement between conduits 110 and 18.

Figure 1:
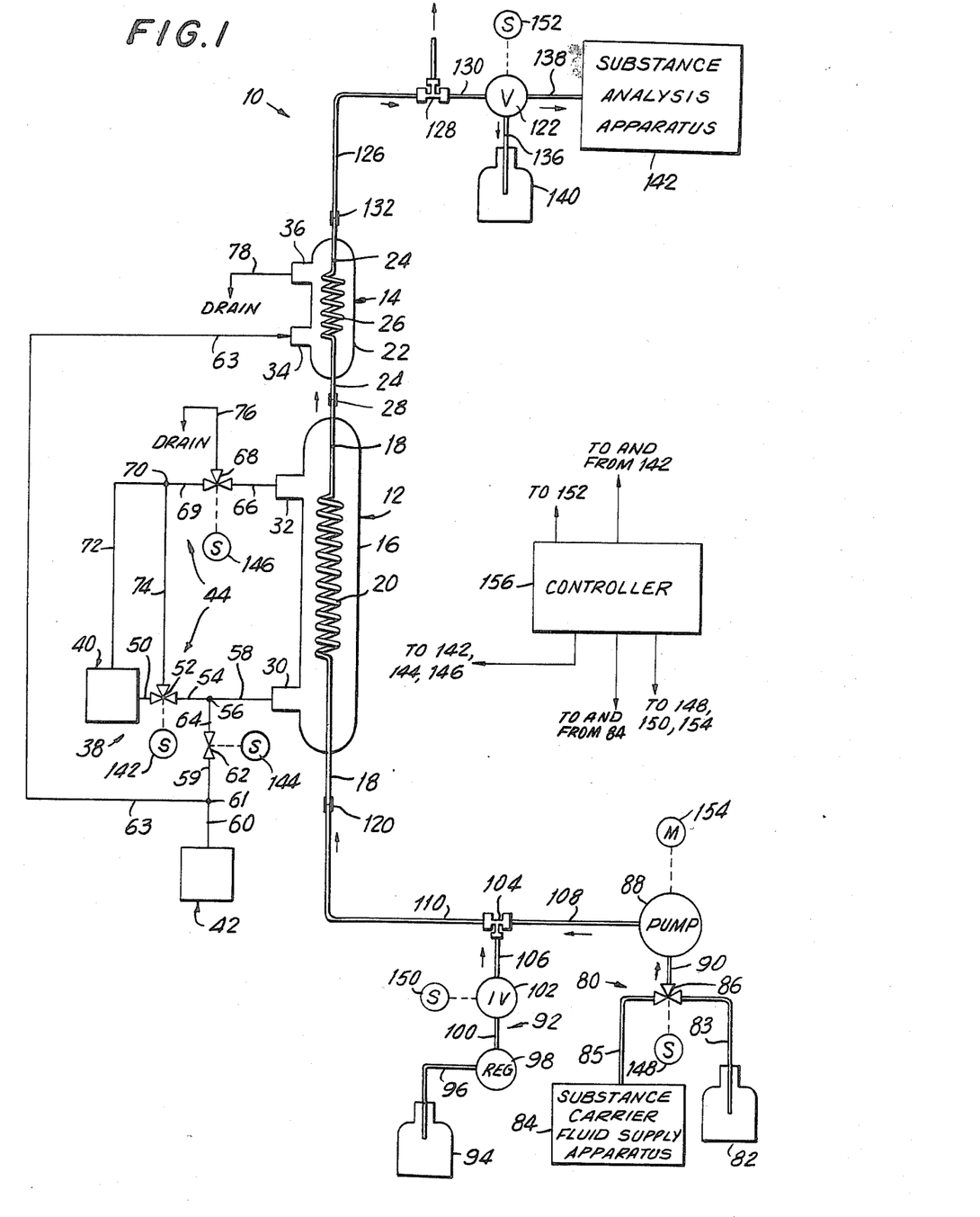

Outlet valve means, preferably taking the form of a multi-port, low dead volume LC valve, are indicated at 122 in FIG. 1. Conduit 126, segmenting fluid removal fitting 128, and conduit 130 connect the outlet of condenser conduit 24 to the inlet of valve 122, and connector 132 is provided as above at the juncture of conduits 24 and 126. Outlet conduits 136 and 138 connect the respective carrier fluid and substance recovery fluid outlets of valve 122 as desired; and may, for example, connect the former to a carrier fluid recovery vessel 140, and the latter to automated substance analysis apparatus, as indicated schematically at 142 for automated, sequential analysis of the substances as contained in the substance recovery fluids. The analysis apparatus 142 may, for example, generally take the form of the chromotographic apparatus disclosed in U.S. Pat. No. 4,274,967 which are operable to automatically quantitatively analyze a plurality of samples as are successively supplied thereto. For such application, a loop sampling valve (not shown) which is, in any event, normally part of an HPLC, would be required for appropriate interfacing, and the operational chromotographic conditions of apparatus 142 would have to be such that the entire substance recovery fluid quantity could be received. Automated substance analysis apparatus 142 do not, in any event, per se form part of this invention.

Valves 52, 62, 68, 86, 102 and 122 are preferably automatically operable under the control, for example, of valve operating solenoids or the like as depicted schematically at 142, 144, 146, 148, 150 and 152, respectively, in operable relationship therewith. Pump 88 is motor driven by a variable speed pump drive motor as indicated schematically at 154 in operable relationship therewith.

An apparatus controller is depicted schematically at 156 and may, for example, take the form of an appropriately programmable micro-processor or like device. Controller 156 is electrically connected to each of the valve operating solenoids 142, 144, 146, 148, 150 and 152 for valve operation as dictated by the controller, and to variable speed pump drive motor 154 to control the speed thereof, with attendant control of the output of pump 88 as, for example, between 0.1 ml/min and 10 ml/min, and provide a stop/start capability for the motor and pump. For continuous flow applications of the apparatus 10 wherein the same are utilized in conjunction with automated substance carrier fluid supply means 84 and automated substance analysis apparatus 142, it will be clear that controller 156 would be electrically connected as indicated to each of the same for overall operational control and synchronization.

A first representative application of the apparatus 10 of FIG. 1 is for the concentration into the substance recovery fluid of a substance as contained in the substance carrier fluid. Examples of the same are a pesticide for the substance, and a solvent such as hexane for both the carrier and recovery fluids.

A requirement for such concentration arises, for example, with regard to the determination of the level of pesticide residue contamination of well water, which can best be accomplished by gas chromatography; it being understood by those skilled in this art, however, that gas chromatographic analysis and well water are basically incompatible, and that direct analysis of water by gas chromatography is generally undesirable. Also, impurities and other analytically interfering materials in the well water could "mask" substance detection. Thus, an initial transfer of the pesticide into a carrier fluid solvent such as hexane which is particularly compatible with gas chromatography is required, and this is readily accomplished by partitioning appropriate like volumes of well water with appropriate like volumes of hexane in which the pesticide is far more soluble. In many instances, however, the resultant pesticide concentration in the hexane is too small, for example one or less parts per billion, to enable effective quantitative analysis by gas chromatography which may not be sufficiently sensitive at such levels. Accordingly, it becomes necessary to materially increase the pesticide concentration in the hexane, thereby materially enhancing the response of the chromatographic detector thereto and permitting effective analysis.

Preferably, of course, this concentration and analysis can be achieved on a consistently accurate and readily reproducible automated basis; and this would be of particular advantage in instances wherein, for example, water samples from a large plurality of wells in a region of suspected pesticide residue water table contamination could be collected and transmitted to a single testing facility for automated analysis.

For such application, and assuming a representative desired pesticide or analyte concentration factor of fifty and a representative apparatus flow rate of 10 ml/min, substance carrier fluid supply apparatus 84 of FIG. 1 would be arranged to supply in intermittent succession to apparatus 10, through conduit 85, valve 86, conduit 90, pump 88, conduit 108, fitting 104, and conduit 110 respectively, a series of different, 100 ml volume pesticide-containing hexane samples; recovery fluid source 82 would contain pure hexane for intermittent supply to apparatus 10 through conduit 83, valve 86, conduit 90, pump 88, and thereafter as above-described; and segmenting fluid source 94 would contain a pressurized, appropriately inert segmenting fluid, for example nitrogen, for segmentation, through conduit 96, regulator 98, conduit 100, valve 102, conduit 106 and segmentation fitting 104, of the respective pesticide-containing hexane, and pure hexane, streams as the same are flowed as described through fitting 104, and for apparatus purging by direct flow through apparatus 10 as described. Controller 156 is configured to cycle, at predetermined time intervals—through control of valves 52, 62 and 68—the operational temperature of vaporizer-collector 12 between, for example, 95° C. which is well above the 69° C. boiling point of the hexane and well below the boiling point of the pesticide and, for example, 24° C. which is approximately the temperature of the tap water from source 42 and well below the boiling point of hexane; and to maintain the temperature of condensor 14 at, for example, 24° C. To this effect, the internal controller of Haake Bath 40 is set at 95° C. whereby, for heating of vaporizer-collector 12 to that temperature, valve 62 is closed by controller 156, and valves 52 and 68 controller-operated to respectively connect conduits 50 and 54, and 66 and 69, thereby circulating the heating fluid from the Haake Bath 40 through vaporizer-collector 12 and back again to the former. For cooling of the vaporizer-condensor 12, to 24° C., valve 62 is opened by controller 156, and valves 52 and 68 controller-operated to respectively connect conduits 50 and 74, and 66 and 76, thereby flowing the cooling water from source 42 through the vaporizer-condensor 12 and therefrom to waste through drain conduit 76, while simply circulating the heating fluid from Haake Bath 40 through the closed loop formed by conduits 50, 74 and 72.

Under these circumstances, and with vaporizer-collector 12 at 95° C., it will be clear that as a nitrogen-segmented, pesticide-containing hexane sample is supplied as described to helically coiled conduit section 20, the hexane will be effectively vaporized with resultant separation of the pesticide therefrom and deposition and accumulation of the pesticide in a band on the interior walls of that conduit section. Although hexane vaporization will be progressive within conduit section 20, the same will be completed well before any of the hexane reaches the upper extremity of that conduit section; thus insuring that no liquid hexane exits conduit section 20 and that none of the pesticide molecules of interest are lost in solution. Of course, the high boiling point of the pesticide vis-a-vis the 95° C. temperature of vaporizer-condensor 12 at this stage insures that no pesticide is lost through vaporization. In addition, the nitrogen segmentation of the hexane samples advantageously functions to break up the surface tension of the hexane as the same vaporizes to materially smooth out that transition and prevent surging of the super-heated hexane which could result in pesticide molecules being carried therewith out of conduit section 20; while the coiled configuration of conduit section 20 advantageously functions to maximize the available heat transfer area per unit length of the vaporizer-condensor 12 vis-a-vis the heating fluid circulating in outer jacket 16, thus maximizing the efficiency of hexane vaporization.

Of course, care must be taken attendant hexane vaporization to insure that the vapor pressure of the pesticide is not raised to a level sufficient to cause pesticide vaporization and loss from conduit section 20. To that effect and in those instances wherein the pesticide of interest has a sufficiently high vapor pressure to cause vaporization and pesticide loss at the operational hexane vaporization temperature during or after hexane vaporization (dryness), "keeper" substances such as high boiling point, viscous silicone oils may be added to the carrier fluid in appropriately low concentrations; it being understood that this addition of the keeper substances will minimize if not totally prevent pesticide loss by preventing a dry state from occurring at the leading edge of the deposited pesticide band in conduit section 20 and insuring that a mixture composition of solvent and/or keeper substance and pesticide exist to prevent pesticide loss of significance.

All of the above contribute not only to insuring the complete separation of the pesticide from the hexane well within coiled conduit section 20, but also to the final deposition of the enriched pesticide in a relatively narrow accumulation or concentration zone or band as indicated at 160 in FIG. 2 at the interface 162 between the boiling but still substantially liquid state hexane, and the vapor state hexane; it being clear that the location of this band within coiled conduit section 20 can, within reasonable limits, be controlled by correlation of the temperature at which vaporizer-collector 12 is maintained with the flow rate at which the hexane sample is flowed therethrough. Thus, for example, it will be clear that increase in the temperature of coiled conduit section 20 will, with the same hexane sample flow rate therethrough, lower band location, and vice versa; while increase in hexane sample flow rate through conduit section 20, at the same section temperature, will raise band location, and vice versa.

The hexane vapor will flow as indicated from coiled conduit section 20 through conduit 18 and conduit 24 to and into the coiled conduit section 26 of condensor 14 for return of the hexane to its liquid state, for ease and safety of subsequent handling, attendant the 24° C. temperature of the latter. Therefrom, the liquid hexane will flow through conduit 24, connector 28, and conduit 126 into and through fitting 128 for removal of the nitrogen segments, and therefrom through conduit 130 to valve 122 which is now operated by controller 156 to direct the pesticide-free liquid hexane through conduit 136 into vessel 140 for re-use or disposal as desired.

Upon the completion of the flow of the 100 ml pesticide-containing hexane sample through the apparatus 10 as described, and with vaporizer-collector 12 retained at 95° C., valve 86 and pump 88 are operated by controller 156 to flow an appropriate quantity, for example 50 ml, of pure hexane from source 82, as segmented by nitrogen at fitting 104, through coiled conduit section 20 of the vaporizer-collector. This will function to in essence pick up and push the trailing edge 163 (FIG. 2) of the deposited pesticide residue somewhat further upward in coiled conduit section 20 to compress and further narrow the width of pesticide band 160 and greatly facilitate subsequent removal of the latter from that conduit section. Of course, none of the pesticide residue is removed from coiled conduit section 20 by this flow of pure, nitrogen-segmented hexane therethrough; and the latter is subsequently re-condensed and handled as described by condensor 14, fitting 128 and vessel 140, respectively.

At the conclusion of the above, and with vaporizer-collector 12 still retained by controller 156 at 95° C., the latter operates to stop pump 88 whereby pure nitrogen from pressurized source 94 will flow through vaporizer-condensor 12 and condensor 14 to thoroughly purge the apparatus 10 of all residual hexane. Thereafter, and with nitrogen purging flow continuing, controller 156 operates the temperature control means 38 to rapidly cool vaporizer-collector 12 to 24° C. and, as this occurs, operates valve 86 and pump 88 to supply pure hexane from source 82 for nitrogen segmentation and supply to the now "cooled," helically coiled conduit section 20 containing the band 160 of the pesticide of interest. As this occurs, the pumping rate of pump 88 is reduced by controller 156 to, for example, 2 ml/min to reduce the size of the hexane segments and insure that the same are neither too large nor fast-moving to dissolve and pick-up the pesticide residue. Since conduit section 20 is now at 24° C., and thus well below the hexane boiling point, the hexane will remain liquid substantially without expansion or contraction attendant its entire transit of that conduit section; and in view of the marked solubility of the pesticide in liquid hexane, the latter will effectively function to pick up the pesticide band 160 as the same very rapidly dissolves into the hexane segments of the flowing stream. Again, the nitrogen segmentation will operate to significant advantage through the mechanical "scrubbing" action of the continually recurring hexane-nitrogen and nitrogen-hexane segment interfaces which will greatly assist in the removal of the pesticide band 160 from the internal wall surface of conduit section 20 for dissolving in the liquid hexane. Thus, the required hexane "pick-up" volume is optimized and, as conclusively established by precisely controlled laboratory testing, complete pesticide band pick-up in the context of the disclosed representative apparatus parameters is assured in at most the first 2 ml of this substance recovery liquid hexane, with attendant accomplishment of the desired 50:1 pesticide concentration vis-a-vis the respective substance carrier and substance recovery hexane volumes.

Controller 156 now operates valve 122 to connect conduits 130 and 138 for a time period predetermined in accordance with apparatus flow rate to enable precisely and only the concentrated pesticide-containing first 2 ml of this liquid hexane quantity to be flowed as described from vaporizer-collector 12 through condensor 14—without adverse effect since the latter is maintained at 24° C.—through fitting 128 for segmentation removal, and through conduit 130, valve 122 and conduit 138 to automated analysis apparatus 142 for automated, gas chromatographic quantitative analysis of the 2 ml of hexane with regard to pesticide level thus, by simple mathematical proportioning, providing the level of pesticide residue contamination in the particular well water sample of interest.

Upon completion of this 2 ml pesticide-containing hexane flow into analysis apparatus 142, controller 156 operates valve 122 to connect conduits 130 and 136 for collection as described in vessel 140 of the immediately following pure hexane quantity, which also has an apparatus purging effect; operates to stop pump 88 to commence the flow of pure nitrogen, only, to and through the apparatus 10 for further purging; and operates temperature control means 38 to rapidly re-heat vaporizer-collector 12 to 95° C. Once the latter is accomplished, controller 156 operates pump 88 to provide pure hexane from source 82, as segmented by the nitrogen from source 94, for flow for a short period of time, for example 15 seconds, through conduit section 20. The output of pump 88 is then increased by controller 156 back to 10 ml/min for flow of the nitrogen segmented hexane through conduit section 20 for a short period of time, for example again 15 seconds, thus establishing even hexane boiling and vaporization. Sample supply apparatus 84 and related system components are then operated as described to supply the next succeeding 100 ml pesticide-containing hexane sample to the apparatus 10 for pesticide concentration and analysis as described. Operation is continuous as described until all samples have been concentrated and analyzed.

A second representative application of the apparatus 10 of FIG. 1 is for the exchange of a substance from the substance carrier fluid to the substance recovery fluid, and the concentration of the substance in the latter. Examples of the same are a pesticide for the substance, a solvent such as methylene chloride for the substance carrier fluid, and a higher boiling point solvent such as hexane for the substance recovery fluid.

A requirement for such exchange again arises, for example, with regard to the determination as described hereinabove of the level of pesticide residue contamination of well water by gas chromatography in instances wherein the pesticide of interest is more highly hydrophillic or water soluble than that heretofore described, and is thus more readily and effectively partitionable in methylene chloride than in hexane; it being understood, however, that hexane is far more compatible with gas chromatographic quantitative pesticide analysis than is methylene chloride. Thus, an exchange of the pesticide from methylene chloride to hexane is dictated.

For such application, as again described by way of relevant example attendant operation on a continuous flow, automated analysis basis, fluid supply apparatus would be arranged to supply in intermittent succession to apparatus 10, as described at a flow rate of 10 ml/minute, 100 ml methylene chloride samples into which the pesticide residue from appropriate like volumes of different well water samples have been partitioned; recovery fluid source 82 would contain pure hexane for intermittent supply as described to apparatus 10; and segmenting fluid source 94 would again contain pressurized nitrogen for solvent streams segmentation and apparatus purging as described.

Under these circumstances, and with controller 156 functioning to maintain vaporizer-collector 12 at, for example, 95° C. which is above the 41° C. boiling point of methylene chloride and the 69° C. boiling point of hexane and, of course, below that of the pesticide, and to maintain the temperature of condensor 14 at, for example 24° C. which is below all relevant boiling points; it will be clear that as a nitrogen-segmented, pesticide-containing methylene chloride sample is supplied to helically coiled conduit section 20 of vaporizer-collector 12, the methylene chloride will be effectively vaporized with resultant ultimate deposition of the pesticide as described in a relatively narrow concentrated zone or band 160 (FIG. 2) on the interior walls of that conduit section. Again, the methylene chloride vapor will then be condensed in condensor 14 for flow as described as a liquid into vessel 140.

As the flow of the pesticide-containing methylene chloride sample through vaporizer-collector 12 is being completed, controller 156 operates to effect the supply as described of an appropriate quantity, again for example 50 ml, of nitrogen-segmented pure hexane from source 82 to and through the coiled conduit section 20 of the vaporizer-collector with resultant hexane vaporization. This functions to in essence move the deposited pesticide residue band 160 somewhat further upward in coiled conduit section 20 and to further narrow the band width by moving the trailing edge 163 closer to leading edge 161; and functions also to purge vaporizer-collector 12 of all remaining methylene chloride vapor by flushing the same therefrom. None of the deposited pesticide is carried from coiled conduit section 20 by this vaporized hexane, and the latter is subsequently condensed in condensor 14 for flow as described as a liquid into vessel 140. As hexane flow is completed, controller 156 operates to supply an appropriate quantity of pure nitrogen as described from pressurized source 94 for hexane-purging flow through coiled conduit section 20 with vaporizer-collector 12 being maintained at 95° C.

With hexane purging completed, but nitrogen flow continuing, controller 156 operates to rapidly lower the temperature of vaporizer-collector 12 to 24° C. and decrease the output of pump 88 through decrease in the speed of motor 154 and, immediately thereafter, to commence the supply as described of nitrogen-segmented pure hexane as a substance recovery fluid from source 82 to the now "cooled" coiled conduit section 20 containing the band 160 of the pesticide of interest. This hexane will remain liquid and will effectively function as described to pick up the pesticide band 160 in plug-like manner as the same very rapidly dissolves into the flowing, nitrogen-segmented hexane stream; it again being made clear that complete pick up of the pesticide by the hexane will occur in the context of the disclosed representative apparatus parameters within, at most, the first 2 ml of liquid hexane flow.

Controller 156 now operates valve 122 to connect conduits 130 and 138 for a time period predetermined in accordance with apparatus flow rate to enable precisely and only the desired concentrated pesticide-containing first 2 ml of this liquid hexane quantity to be flowed as described from vaporizer-collector 12 to automated analysis apparatus 142 for quantitative pesticide analysis. Thus, both solvent exchange and pesticide concentration are effectively accomplished by the apparatus 10 of the invention attendant the same operational cycle. Again, flow of the pesticide-containing 2 ml of hexane into analysis apparatus 142 is followed as described under the direction of controller 156 by flow of the remaining liquid hexane quantity into vessel 140, the flow of pure nitrogen through apparatus 10 to purge the same of residual hexane, and the rapid reheating of vaporizer-collector 12 to, in this instance, 95° C. Introduction in turn of the succeeding pesticide-containing methylene chloride samples follows for processing and analysis as described.

Figure 3:
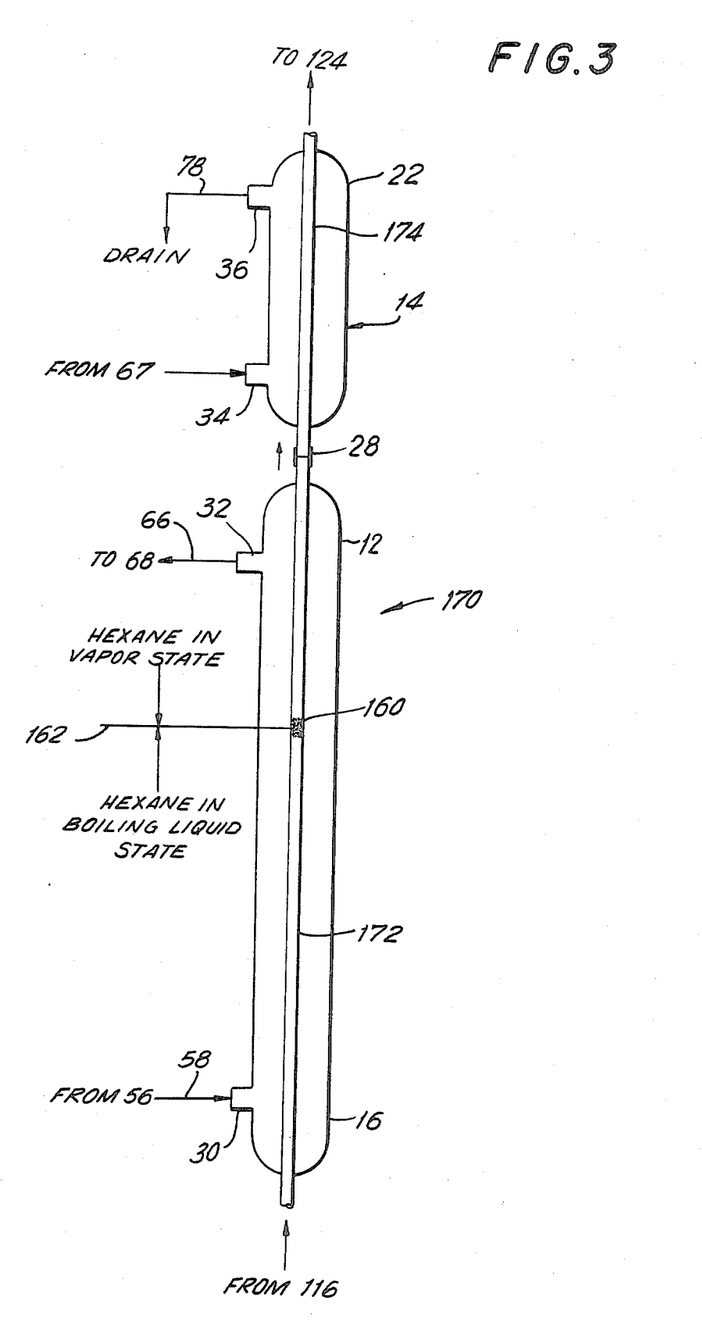

A second embodiment of apparatus constructed and operative in accordance with the teachings of this invention is depicted in part as indicated generally at 170 in FIG. 3, and may be understood to be substantially identical to the embodiment of FIG. 1 with the exception that the helically coiled conduit sections 20 and 26 of the vaporizer-collector 12 and condensor 14 of apparatus 10 of FIG. 1 are replaced in each instance in the apparatus 170 of FIG. 3 by straight lengths of concentrating and condensor column conduits 172 and 174 of the same diameter as those of FIG. 1 which respectively extend as shown generally centrally of outer jackets 16 and 22. Of course, utilization of straight, rather than helically coiled, conduit sections as described to form the concentrating and condensor columns requires substantial increase in the lengths thereof to achieve the same heat transfer conduit surface areas, and in the overall lengths of the outer jackets 16 and 22 which accommodate the same; and this is made clear by FIG. 3 wherein the respective lengths of conduits 172 and 174, and the outer jackets 16 and 22 will readily be seen to be substantially greater than those of the like components in FIG. 1. Operation of apparatus 170 is virtually identical to that as described for apparatus 10; and, to that effect, a band 160 of concentrated deposited pesticide is depicted in conduit 172 of FIG. 3 at a representative location.

Figure 2:
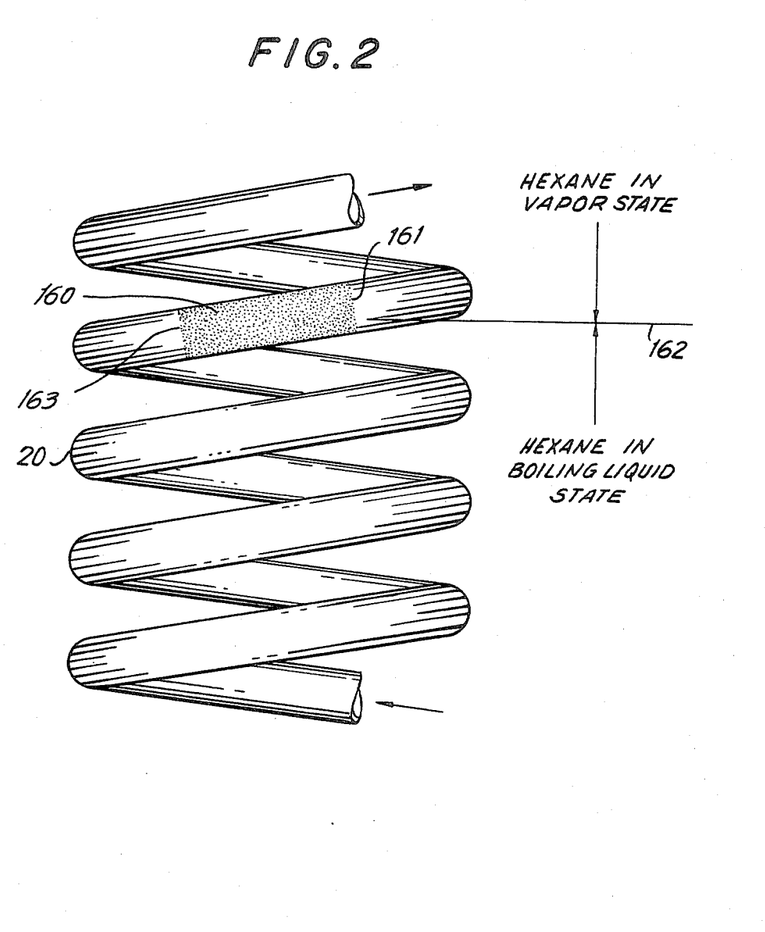

Although the embodiments of FIGS. 1 and 2, and FIG. 3, are disclosed as operable, to full advantage in accordance with the teachings of this invention, on an automated basis in conjunction with automated sample supply and sample analysis apparatus 84 and 142, respectively, it will be clear that the same are by no means limited thereto, but rather, may alternatively be operated on a batch basis with equally high efficiencies of substance exchange and/or concentration. For batch basis operation, sample supply apparatus 84 would be replaced by a simple container of the substance carrier fluid, and substance analysis apparatus 142 replaced, for example, by appropriate fraction collector means wherein the desired quantity of the substance recovery fluid could be collected in a small bottle. Following collection, the substance recovery fluid volume of interest could be mixed, as by shaking, to insure the homogeneity thereof, and re-sampled in any appropriate manner for introduction into an appropriate chromatographic analysis device. Batch basis operation as described could enable the elimination of segmentation fluid removal fitting 128 since the segmentation fluid would naturally escape upon recovery fluid collection.

Figure 4:
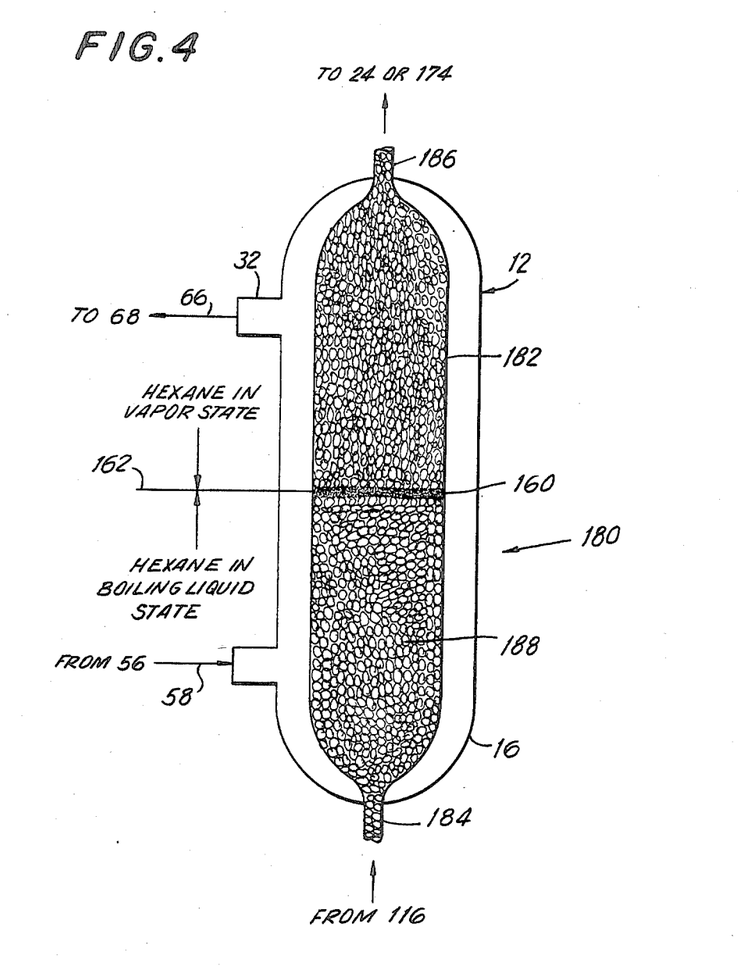

A third embodiment constructed and operative in accordance with the teachings of this invention is depicted in part as indicated at 180 in FIG. 4 and differs structurally from the embodiments of FIGS. 1 and 2, and 3, in that the conduit 18 and coiled conduit section 20, or the straight conduit 172 as the case may be, are replaced within outer jacket 12 by a generally cylindrical separating chamber 182 of substantially greater diameter, and which includes protruding inlet and outlet conduits 184 and 186. The separation chamber 182 is packed as shown by a matrix of beads or the like as indicated at 188 and which function on the nature of boiling chips to present a greatly increased overall heat transfer surface area per unit length of the outer jacket 16 and significantly promote solvent vaporization. In addition, the beads 188 operate to preserve the integrity of the pesticide band 160—which is again formed and compressed as described upon solvent vaporization at the interface 162 between the boiling liquid state solvent and the vapor state solvent—during the pesticide wash-out or recovery step, thus promoting efficient, plug-like pesticide flow out of the concentrating column, although a relatively greater volume of substance recovery fluid may be required to accomplish the same. The condensor 14 (not shown) for the apparatus 180 of FIG. 4 may take either the form of FIG. 1 or that of FIG. 3, but with substantially smaller I.D. conduits to prevent broadening of the pesticide band, with resultant increase in back pressure and attendant decrease in operational rate.

As currently contemplated, apparatus 180 of FIG. 4 is for operation on a batch basis with non-segmented substance carrier and substance recovery fluid flow; it being clear to those skilled in this art that, for example, nitrogen segmentation as described hereinabove of the pure hexane stream from source 82 during the pesticide wash-out or recovery step could, in combination with the matrix of beads 188, have adverse effect upon the integrity of the pesticide band 160 as the same is recovered by the liquid hexane. Thus batch-basis operation of the apparatus 180 would be generally the same as that described hereinabove for apparatus 10 and 170, but without the segmenting fluid supply means 92.

A preferred material for the respective components of the vaporizer-collector 12 and condensor 14 of all of the disclosed embodiments, and for the glass beads 188 of the embodiment of FIG. 4, would be annealed Pyrex glass which is advantageously relatively inert, highly heat-resistant, readily available and inexpensive, non-catalytic, readily fabricatable by long-known methods, and transparent. However, for application wherein high thermal conductivity is a major consideration, appropriate metals could be utilized for the concentrating column in vaporizer-collector 12 and the condensor column in condensor 14; it being understood that such metals would have to be inert to the substances and solvents in question, capable of withstanding the operational temperatures of the apparatus without critical change in dimension, and incapable of inducing lability in the substances in question due to catalytic degradation at those operational temperatures. Thus, for example, aluminum could be considered for applications involving organic solvents and pesticides.

Representative pesticides for exchange and/or concentration by the apparatus and method of the invention, and with which "keepers" would most probably be utilized as described, are BHC isomers, Aldrin, DDT isomers, parathion, and malathion. For operation as above described without "keepers," representative pesticides would most probably include only those with vapor pressures equal to or greater than that of p,p'-DDT, and would include p,p'-DDT, Ethion, Mirex, and Methoxychlor. Representative solvents other than hexane and methylene chloride would include acetone and many of the alcohols.

Although disclosed as advantageously functioning to combine both the substance exchange and concentration functions, it is clear that the apparatus and method of the invention may effectively operate to exchange a substance between solvents in virtually any conceivable, reasonable solvent volume ratio, including unity or those which would constitute a dilution. Also, although disclosed as operable upon substances taking the form of pesticides with regard to substance and recovery fluids taking the form of solvents, it is clear that those substances and fluids are representative, only of extremely wide ranges of the same which may be effectively operated upon and with by the apparatus and method of the invention as described. Thus, for example, the substances could take the form of organic pollutants such as phenols or PCB's, or trace metals such as Pb, Zn, Cu, Cr or the like. In like manner, the substance carrier and recovery fluids need by no means be restricted to solvents, but rather, can include virtually any liquid which can carry the substance of interest, either in solution or suspension, and which can be operated upon as described by the apparatus and method of the invention. In addition, it will be clear that the substance exchange and/or concentration functions of the apparatus and method of the invention are by no means limited to applications involving subsequent substance analysis. Of course, all specified temperatures, flow rates and volumes and the like are representative and not limitative.

Various changes may be made in the disclosed embodiments of this invention without departing from the spirit and scope thereof as defined by the appended claims.

What is claimed is:

1. Apparatus for the automated sequential formation and analysis in turn of each of a series of substance-containing recovery fluid volumes through use of automated fluid volume supply apparatus and automated fluid volume analysis apparatus and including, separation chamber means having an inlet and an outlet, means for automatically flowing substance-containing carrier fluid volumes in turn from said automated fluid volume supply apparatus into said separation chamber means through said inlet, means for concomitantly automatically controlling the temperature of said separation chamber means to be effective to vaporize said carrier fluid and ineffective to vaporize said substance with resultant separation of said substance from said carrier fluid at a separation zone in said separation chamber, said separation chamber means including means for accumulating the thusly separated substance in a band at said separation zone, means for flowing the substance-free carrier fluid out of said separation chamber means through said outlet, means for correlating the flow rate of said substance carrier fluid into said separation chamber means and the temperature of said separation chamber means to determine the location of said accumulated substance band in said separation chamber means, means operable subsequent to the flow of each of said substance-containing carrier fluid volumes into said separation chamber means to automatically flow a substance recovery fluid volume from said automated fluid volume supply apparatus into said separation chamber means through said inlet, means for concomitantly automatically controlling the temperature of said separation chamber means to be ineffective to vaporize said substance recovery fluid or said substance with resultant pick-up of the thusly accumulated substance band by the substance recovery fluid and means for automatically flowing at least a portion of each of the substance-containing recovery fluid volumes in turn to said automated analysis apparatus for analysis thereby.

2. In apparatus as in claim 1 further comprising, means for automatically segmenting each of said substance carrier fluid volumes and each of said substance recovery fluid volumes with a segmenting fluid prior to the respective flows thereof into said separation chamber means, thereby promoting substance separation from said carrier fluid and substance pick-up by said recovery fluid.

3. In apparatus as in claim 1 further comprising, means operable subsequent to the flow of each of said substance-containing carrier fluid volumes into said separation chamber means and prior to the flow of each of said recovery fluid volumes thereinto to automatically flow a non-substance containing volume of said carrier fluid through said separation chamber means to compress the thusly separated and accumulated substance band therein and facilitate the recovery thereof by said substance recovery fluid volume.

4. Apparatus for separating a substance from a substance carrier fluid comprising, separating chamber means having an inlet and an outlet, means for flowing a stream of a substance-containing carrier fluid into said separation chamber means through said inlet, means for concomitantly controlling the temperature of said separation chamber means to be effective to vaporize said carrier fluid and ineffective to vaporize said substance for separation of said substance from said carrier fluid at a separation zone in said separation chamber means, said separation chamber means including means for accumulating the thusly separated substance in a band at said separation zone, means for flowing the substance-free carrier fluid out of said separation chamber means through said outlet, means for correlating the temperature of said separation chamber means and the flow rate of said substance-containing carrier fluid thereinto to determine the location of said accumulated substance band in said substance accumulating means, and means for subsequently recovering the thusly separated and accumulated substance band from said separation chamber means, said substance recovery means comprising, means for flowing a stream of a substance recovery fluid in which said substance is soluble into said separation chamber means through said inlet, means for concomitantly controlling the temperature of said separation chamber means to be ineffective to vaporize said substance recovery fluid or said substance with resultant pick-up of said substance by said substance recovery fluid, and means for flowing the substance-containing recovery fluid out of said separation chamber means through said outlet.

5. In apparatus as in claim 4 further comprising, means for segmenting said substance carrier fluid and said substance recovery fluid with a segmenting fluid prior to the respective flows thereof into said separation chamber, thereby promoting substance-carrier fluid separation in said separation zone, and promoting substance band pick-up by said substance carrier fluid.

6. In apparatus as in claim 4 further comprising, means for flowing non substance-containing carrier fluid through said separation chamber means to compress the thusly separated and accumulated substance band therein prior to substance recovery fluid flow therethrough.

7. In apparatus as in claim 4 further comprising, means for flowing a purging fluid through said separation chamber means to purge the same of said substance carrier fluid prior to substance recovery fluid flow therethrough.

8. In apparatus as in claim 4, wherein, said separation chamber means comprise a conduit, and said means for accumulating the thusly separated substance at said separation zone comprise a matrix disposed within said conduit.

9. In apparatus as in claim 8 wherein, said matrix comprises a plurality of beads.

10. In apparatus as in claim 4 wherein, said separation chamber means comprise a conduit having an internal wall, and said means for accumulating the thusly separated substance at said separation zone comprise the internal wall of said conduit.

11. In apparatus as in claim 10 wherein, said conduit comprises a generally helical conduit portion which 12. In apparatus as in claim 10 wherein, said conduit comprises a generally straight conduit portion which defines said separation zone.

* * * * *